United States Patent [19]

Fischer et al.

[11] 3,950,529

[45] Apr. 13, 1976

[54] AMINO ACID FORMULATIONS FOR PATIENTS WITH LIVER DISEASE AND METHOD OF USING SAME

[75] Inventors: Josef E. Fischer, Boston, Mass.; Norman N. Yoshimura, Woodland Hills, Calif.; Thomas L. Westman; Fred H. Deindoerfer, both of Northridge, Calif.

[73] Assignees: Massachusetts General Hospital, Boston, Mass.; American Hospital Supply Corporation, Evanston, Ill.

[22] Filed: Feb. 3, 1975

[21] Appl. No.: 546,689

[52] U.S. Cl. .............. 424/273; 424/274; 424/319
[51] Int. Cl.² ............ A61K 31/415; A61K 31/40; A61K 31/195
[58] Field of Search .................... 424/273, 274, 319

[56] References Cited
UNITED STATES PATENTS

| | | | |
|---|---|---|---|
| 2,666,013 | 1/1954 | Ferguson, Jr. | 424/319 |
| 3,256,095 | 6/1966 | Crosby | 424/319 |
| 3,697,287 | 10/1972 | Winitz | 424/319 |
| 3,764,703 | 10/1973 | Bergstrom et al. | 424/319 |
| 3,773,930 | 11/1973 | Mohammed et al. | 424/274 |
| 3,793,450 | 2/1974 | Schnell | 424/319 |

*Primary Examiner*—Donald B. Moyer

[57] ABSTRACT

Amino acid formulations for administration to human patients with liver disease comprise mixtures of essential amino acids combined in novel relative proportions, and preferably also include non-essential amino acids. In particular, the combined molar proportions of isoleucine, leucine, and valine are from 40 to 300 times the molar proportion of tryptophan and from 15 to 135 times the molar proportion of phenylalanine, or phenylalanine and tyrosine. The formulations may be adapted for either intravenous or oral administration, but the preferred method of administration is by hyperalimentation infusion. The formulations and method can be utilized to provide nutritional support for liver diseased patients while reducing the incidence and severity of hepatic encephalopathy, and/or as primary therapy for treatment of hepatic encephalopathy.

14 Claims, No Drawings

AMINO ACID FORMULATIONS FOR PATIENTS WITH LIVER DISEASE AND METHOD OF USING SAME

BACKGROUND AND PROBLEM

Intravenous amino acid solutions are known and are approved for clinical administration to patients requiring intravenous nutrition. They are usually administered along with glucose, fat, electrolytes, and vitamins. The present commercial intravenous amino acid solutions are formulated in accordance with the amino acid requirements of man as delineated by William C. Rose and associates. See, Rose, *Fed. Proc.* 8, 546 (1949); Rose et al., *J. Biol. Chem.*, 217, 987 (1955). U.S. Pat. No. 3,764,703 discloses the use of mixtures of essential amino acids combined in proportions according to the pattern of Rose for administration to patients suffering from reduced kidney function, uremia. According to this patent, the essential amino acids may be administered for the treatment of uremic conditions either intravenously or orally, with resultant lowering of blood urea nitrogen and increased nitrogen retention.

U.S. Pat. No. 3,832,465 discloses intravenous infusion solutions of amino acids containing both essential and nonessential amino acids, which are characterized by having at least 40%, and preferably from 42 to 68%, of the total amino acids comprising the branched chain amino acids, leucine, isoleucine, and valine. It is stated that the branched chain amino acids are metabolized by major pathways not involving the liver, and that therefore they can be intravenously administered in larger proportions than those amino acids dependent on the metabolic action of the liver.

Prior to the present invention, as far as is known, no specially formulated amino acid mixtures have been proposed for administration to liver diseased patients either for therapeutic effects or for nutritional purposes. Malnutrition is a serious problem with such patients. The patient with cirrhosis generally eats poorly, and such patients are usually placed on protein-restricted diets. Liver disease interferes with normal protein utilization. Moreover, encephalopathy leading to coma and death is associated with advanced cirrhosis and other serious liver disease. By restricting protein intake, the tendency of the liver diseased patients to develop hepatic encephanlopathy may be reduced. However, such limitation of protein intake further contributes to the malnutrition of the patient.

Rose pattern intravenous solutions of amino acids have been administered to liver diseased patients both for nutritional support and experimentally for study of the effect on the patient's plasma amino acid levels. Such studies have shown that the content of amino acids in the plasma of liver diseased patients is seriously distorted, the branched chain amino acids (isoleucine, leucine, and valine) being lower than normal, while methionine and the aromatic amino acids phenylalanine and tryptophan are higher than normal. See Fischer et al., *Am. J. Surg.*, 127, 40 (Jan. 1974), and references cited therein. The amino acid formulations administered by Fischer et al. included solutions containing only essential amino acids, as well as solutions containing both essential and nonessential amino acids. The plasma levels of the branched chain essential amino acids and methionine were consistently decreased, while there was a consistent elevation above normal of phenylalanine and methionine. However, the tryptophan levels were near normal or only slightly elevated. With the mixture of essential and nonessential amino acids, tyrosine was considerably above the normal level, and was found to be elevated, although to a lesser extent, even with the mixture containing only the eight essential amino acids.

An attempt was made to increase the low plasma levels of branched chain amino acids by increasing the amount infused up to two and one half times the minimal daily requirements recommended by Rose for isoleucine, leucine, and valine. Such high level infusion of branched chain amino acids, however, failed to correct the low concentrations of these amino acids in the patients' plasma. The metabolic consequence of low plasma levels of branched chain amino acids is not known, nor has anyone previously proposed a relationship between plasma levels of branched chain amino acids and hepatic encephanlopathy.

It has been suggested that an excess of phenylalanine may inhibit the transport of tyrosine to the brain. Guroff et al., *J. Biol. Chem.* 237, 803 (1962). Further, it is known that tyrosine is important for the synthesis of some of the normal catecholamine neurotransmitters in the brain. It has also been suggested that the level of serotonin in the brain may be related to the association between plasma tryptophan, as opposed to plasma phenylalanine, tyrosine, and the branched chain amino acids. Fernstrom, et al., *Science*, 178, 414 (1972). However, earlier studies tended to establish that the principle factor modulating brain tryptophan was the ratio of plasma tryptophan to the sum of all of the plasma amino acids. See Perez-Cruet et al., *Nature*, 248, 693 (1974).

In accordance with the present invention, the amount administered of phenylalanine alone, or phenylalanine and tyrosine in combination, or tyrosine alone is controlled in relation to the total of the essential branched chain amino acids, specifically isoleucine, leucine, and valine to achieve metabolically acceptable levels of plasma phenylalanine and tyrosine. It appears that the formulations of the present invention permit adequate transfer of tyrosine to the brain, and that there is no serious inhibition of such transport due to excessive plasma phenylalanine. Further, the amount of phenylalanine administered may be reduced, or in some embodiments eliminated entirely, if the phenylalanine in the amino acid mixture is partially replaced by tyrosine. Such replacement is limited by the low water solubility of tyrosine. The tyrosine can be supplemented by more water soluble tyrosine derivatives, providing the derivative is convertible by the body to tyrosine.

The experimental work leading to the present invention has also indicated that the relative proportions of the essential branched chain amino acids should be controlled in relation to the proportion of tryptophane administered. By proper balancing of the proportions of isoleucine, leucine, and valine to tryptophan, it is believed that the transfer of excessive tryptophan to the brain can be avoided. This is desirable since tryptophan is converted by the brain to serotonin, which would be expected to complicate hepatic encephalopathy. It therefore appears that the quantity of amino acid administered for nutritional utilization by the patient can be significantly increased while therapeutically maintaining normal brain function. In general, all of the plasma amino acids may compete with the plasma tryptophan for transport to the brain. However, what seems to be of importance for the purpose of the present invention is that phenylalanine and tryosine are relatively less competitive with tryptophane for entry into the brain compared to the branched chain essential amino acids.

It should be understood that the foregoing mechanisms are not known with complete certainty. Further, diseased livers do not respond predictably in all cases. Nevertheless, the available experimental evidence, strongly indicates that administration of the amino acid formulation of this invention can be expected to therapeutically reduce the incidence and severity of hepatic encephalopathy, while providing more nearly adequate nutritional support for the patients suffering from liver disease. The treatment of hepatic encephalopathy should also be clinically attainable. Moreover, by achieving more nearly adequate nutrition, while avoiding the complications of encephalopathy and coma, an opportunity is provided for improved liver function to develop. It is known that the liver has remarkable power to hypertrophy or regenerate. Consequently, if the patient can be maintained over a sufficient period of time with adequate nutrition, the liver may repair and fully recover.

The formulations of this invention may include both essential and nonessential amino acids, or only essential amino acids, but the inclusion of some nonessential amino acids is desirable. With respect to nutritional support, resultant plasma amino acid levels, brain function, and therapeutic benefits there is a complex interrelationship between the amino acid formulations of this invention. In addition to the considerations discussed above, therefore, the relative proportions of all of the amino acids incorporated, essential and nonessential, including amino acids which may be optionally included, are specified in terms of their respective molar ranges.

DETAILED DISCLOSURE

The amino acids used in practicing the present invention are preferably pure crystalline amino acids. In general, the amino acids should be in their L-form, rather than the D-form, or a mixture of D and L. Also, in general, the amino acids are employed as free amino acids rather than as amino acid salts or derivatives. L-lysine acetate may be used, and derivatives of L-tyrosine which are convertible to tyrosine by the body.

Mixtures of essential and nonessential amino acids prepared in accordance with the present invention for administration to human patients with liver disease should contain the amino acids in interrelated proportions. Desirable relative internal proportions are defined by the following molar ranges:

| Amino Acids | Molar Ranges |
| --- | --- |
| L-isoleucine | 0.0549–0.0823 |
| L-leucine | 0.067–0.101 |
| L-valine | 0.0574–0.0861 |
| L-tryptophan | 0.000816–0.00441 |
| L-phenylalanine | 0–M |
| L-tyrosine | 0–0.003 |
| L-lysine | 0.0333–0.05 |
| L-methionine | 0.00491–0.0147 |
| L-threonine | 0.0228–0.0454 |
| L-alanine | 0.0686–0.103 |
| L-arginine | 0.0275–0.–413 |
| L-histidine | 0.0124–0.0186 |
| L-proline | 0.0556–0.0834 |
| L-serine | 0.0152–0.0571 |
| glycine | 0.0451–0.144 |
| L-aspartic acid | 0–0.0451 |
| L-glutamic acid | 0–0.0702 |
| L-ornithine | 0–0.0382 |

-continued

| Amino Acids | Molar Ranges |
| --- | --- |
| L-cysteine | 0–0.00228 |

Optionally, part of the L-methionine in the above formulation may be replaced by D-methionine, a mixture of DL-methionine being used on an equivalent basis to L-methionine. D-methionine has approximately 75% of the nutritional value of L-methionine, which percentage can be used to determine the desirable equivalent range for a mixture of DL-methionine. However, it is preferred to employ only L-methionine.

Certain other amino acids can be used in modified forms. For example, the lysine can be advantageously used in the form of its acetate salt (L-lysine acetate). Also, it is convenient to incorporate the cysteine in the form of its hydrochloride salt (L-cysteine·HCl·$H_2O$).

In the above formulation, the upper limit of the molar range for phenylalanine is indicated by the letter "M". Where the formulation includes no tyrosine, M will be equal to 0.009, that is, the molar range for phenylalanine will be 0–0.009. When tyrosine is incorporated, the amount of phenylalanine is correspondingly reduced. More specifically, M will be equal to 0.009 minus the respective molar amount of free tyrosine. For example, when the amount of tyrosine in the formulation is equal to 0.003, M will be 0.006. Both phenylalanine and tyrosine should not be omitted. The total of phenylalanine and tyrosine should be equal to at least 0.002 moles in relation to the molar proportions set out above.

As indicated by the lower limit of "0", several of the other amino acids listed in the above formulation are optional, that is, they can be omitted completely. These optional amino acids include aspartic acid, glutamic acid, ornithine, and cysteine. Phenylalanine may also be omitted in some embodiments if tyrosine is included. In most formulations, some phenylalanine also will be included, at least 0.00266 moles on the same basis, that is, a range of 0.00266–0.009 for phenylalanine if no tyrosine is included, or 0.00266-M if tyrosine is present.

It will be understood that in addition to the amino acids, the formulation may include preservatives or stabilizers, as required, such as sodium bisulfite, asocrbic acid (vitamin C), or other compatible preservative agents. Nitrogen gas may also be used to preserve the solution.

In accordance with the present invention, the respective molar proportions of isoleucine, leucine, valine, tryptophan, and phenylalanine (or phenylalanine and tyrosine) should be selected to provide certain ratios of these amino acids. More specifically, the ratio of the combined molar proportions of isoleucine, leucine, and valine to (a) the molar proportion of tryptophane should be within the numerical range from 40 to 300, and to (b) the molar proportion of phenylalanine, or the combined molar proportion of phenylalanine and tyrosine, should be within the numerical range from 15 to 135. Although, the complete optimization of the formulation within the specified ranges has not yet been fully defined, nutritionally and/or therapeutically applicable molar proportions for the total of the branched chain amino acids (isoleucine, leucine, and valine) to the molar proportion of tryptophan is from 50 to 90, and to the molar proportion phenylalanine, or phenylalanine and tyrosine, from 30 to 50.

The formulations are desirably free of ammonia. When prepared from crystalline amino acids, the resultant formulation will be low in free ammonia. In general, the formulations preferably contain less than 2 millimoles of ammonia per each 800 millimoles of amino acids, including all of the amino acids present (essential and nonessential).

The formulations may be advantageously prepared in the form of sterile aqueous solutions adapted for intravenous administration. In accordance with known practice for such solutions, the liver disease amino acid solutions will be sterile, pyrogen-free, and at a suitable pH for intravenous administration. The most desirable pH for the solution may vary depending on whether the amino acid solution is to be mixed with an intravenous dextrose solution before administration, but, in general, the pH of the amino acid solution can range from 5.0 to 7.8. Where the patient with liver disease is being fed a protein-restricted diet and the intravenous amino acid solution is to be used as a supplement to such diet, in some cases, peripheral intravenous infusion techniques may be used. However, the preferred technique involves administration into a central vein, which is a procedure known clinically as hyperalimentation. In this technique, the infusion is made into the central vein through a catheter. For example, either a subclavian or internal jugular indwelling catheter may be used.

Amino acid infusion solutions prepared for hyperalimentation use with liver diseased patients can contain from 2 to 9 weight percent of total amino acids based on the solution. In preferred embodiments, which can be used for total parenteral nutrition, it is believed that the optimum concentration of total amino acids will be from 3 to 5 weight percent based on the solution as prepared for infusion. Where the amino acid solution is prepared in more concentrated form, it can be mixed with other nutrient-containing solutions (viz. aqueous glucose) to prepare an infusate solution of the preferred amino acid concentration.

With intravenous solutions prepared as described above, it is expected that full protein nutrition can be provided by administration from about 1 to 3 liters of solution per patient during each 24 hours. The maximum amount which may be administered will depend on the amino acid tolerance of the particular patient. While the formulation of the present invention is capable of reducing the incidence and severity of hepatic encephalopathy, the desirable clinical procedure will be to begin the infusion at a daily level below full protein nutrition, and gradually increase the amount administered. For example, the administration can be started at levels equivalent to about 20 to 25 grams protein per day (24 hrs.), and then increased to at least 40 to 50 equivalent grams protein per day, providing the patient is tolerating the infusion. It is expected that the average patient will be able to tolerate at least the equivalent of 50 grams protein per 24 hrs., and in some cases, much higher administration levels up to as high as 100 to 140 grams protein equivalents may be feasible. For the purpose of the present invention, and as known to biochemists, the equivalency of amino acids to protein can be calculated by determining the total grams of amino acid nitrogen, and then multiplying this amount by 6.25 to obtain the grams of equivalent protein.

One formulation, including no tyrosine, which may be prepared as a concentrated infusion solution will now be described. The concentrations are given in moles per liter of solution. If the formulation is employed for oral administration, the relative concentrations indicated should be maintained, that is, the oral formulation will have the same amino acids in the same respective molar concentrations or ranges.

The formulation is as follows:

| Amino Acids | Concentrations (moles/l. soln.) |
| --- | --- |
| L-isoleucine | 0.059–0.0823 |
| L-leucine | 0.067–0.101 |
| L-valine | 0.0574–0.0861 |
| L-tryptophan | 0.000816–0.00441 |
| L-phenylalanine | 0.00444–0.0133 |
| L-lysine | 0.0333–0.0500 |
| L-methionine | 0.00491–0.0147 |
| L-threonine | 0.0228–0.0454 |
| L-alanine | 0.0686–0.103 |
| L-arginine | 0.0275–0.0413 |
| L-histidine | 0.0124–0.0186 |
| L-proline | 0.0556–0.0834 |
| L-serine | 0.0152–0.0571 |
| glycine | 0.0451–0.144 |
| L-cysteine | 0–0.00228 |

The amino acid formulation of this invention as designed for use with liver disease patients contains the amino acids, (both essential and nonessetial) in proportions widely different from the amino acid content of any naturally occuring proteins. Further, the relative proportions are markedly different than the amounts of essential amino acids heretofore believed to be necessary for proper nutrition. The comparison is indicated by the following table, where the essential amino acids are shown in the first column as they would be in accordance with the pattern of Rose. The next column illustrates a preferred formulation of the present invention.

| | Comparison with Rose's Pattern for Essential Amino Acids | |
| --- | --- | --- |
| Amino Acid | Rose* | Illustrative Liver Disease Formulation |
| Isoleucine | 110 | 216 |
| Leucine | 173 | 263 |
| Valine | 126 | 201 |
| Tryptophan | 39 | 18 |
| Phenylalanine | 173 | 24 |
| Lysine | 126 | 146 |
| Methionine | 173 | 24 |
| Threonine | 79 | 108 |

*In mg./g. total amino acids.

Specific formulations for practicing the present invention are set out in the following examples.

EXAMPLE I

A sterile, non-pyrogenic, stable solution suitable for intravenously infusing into liver diseased patients is prepared from pure crystalline amino acids, which are dissolved in distilled water in the following concentrations:

| Amino Acid | g./l. | | mole/l. |
| --- | --- | --- | --- |
| L-isoleucine | 9.0 | | 0.0686 |
| L-leucine | 11.0 | | 0.0838 |
| L-valine | 8.4 | | 0.0717 |
| L-tryptophan | 0.75 | | 0.00367 |
| L-phenylalanine | 1.0 | | 0.00605 |
| L-lysine acetate | 8.6 | (base, 6.09) | 0.0417 |

| Amino Acid | g./l. | | mole/l. |
|---|---|---|---|
| L-methionine | 1.0 | | 0.0067 |
| L-threonine | 4.5 | | 0.0378 |
| L-alanine | 7.65 | | 0.0858 |
| L-arginine | 6.0 | | 0.0344 |
| L-histidine | 2.4 | | 0.0155 |
| L-proline | 8.0 | | 0.0695 |
| L-serine | 5.0 | | 0.0476 |
| glycine | 9.0 | | 0.120 |
| L-cysteine.HCl.H$_2$O | 0.2 | (base 0.14) | 0.00114 |

In the foregoing formula, the ratio of the essential branched chain amino acids to phenylalanine is about 37 and to tryptophan is about 61.

To this solution is added 1.152 g./l. of 85% phosphoric acid to adjust the pH to a more physiological pH (approx. 6.8), and to serve as a source of phorphorous, an important element for good nutrition. The volume is then brought to the desired volume with distilled water. Sodium bisulfite U.S.P. grade, 1.0 g./l., is added and stirred until dissolution is complete. Two grams of activated charcoal is then added and stirred for an additional 10 minutes. The solution is then filtered and filled into appropriate containers for intravenous fluids and steam sterilized at 250°F. for 10 minutes.

EXAMPLE II

If a formulation of amino acids for liver diseased patients is desired which contains only essential amino acids, the nonessential amino acids in the intravenous solution of Example I can be omitted. The same relative proportions of the essential amino acids (isoleucine, leucine, valine, tryptophan, phenylalanine, lysine, methionine, and threonine) will be present; and the solution will be prepared in the same manner. Preferably, however, arginine, histidine, and cysteine are also included in the indicated relative proportions with the eight essential amino acids.

EXAMPLE III

Following the procedure of Example I, an alternate amino acid formulation for liver disease therapy is provided in which the molar ratio of the sum of valine, leucine, and isoleucine to (a) phenylalanine plus tyrosine and (b) tryptophan is 50 to 275, respectively.

| Amino Acid | g./l. | | mole/l. |
|---|---|---|---|
| L-isoleucine | 9.0 | | 0.0686 |
| L-leucine | 11.0 | | 0.0838 |
| L-valine | 8.4 | | 0.0717 |
| L-tryptophan | 0.2 | | 0.000816 |
| L-phenylalanine | 0.73 | | 0.00444 |
| L-lysine acetate | 8.6 | (base, 6.09) | 0.0417 |
| L-methionine | 1.0 | | 0.0067 |
| L-threonine | 3.4 | | 0.0285 |
| L-alanine | 9.18 | | 0.103 |
| L-arginine | 7.1 | | 0.0408 |
| L-histidine | 2.5 | | 0.0161 |
| L-proline | 8.0 | | 0.0695 |
| L-serine | 1.6 | | 0.0152 |
| glycine | 3.4 | | 0.0451 |
| L-cysteine.HCl.H$_2$O | 0.4 | | 0.00228 |

EXAMPLE IV

Following the procedure of Example I, an alternate amino acid formulation for liver disease therapy is prepared from the following pure crystalline amino acids and in the following concentrations:

| Amino Acid | g./l. | | mole/l. |
|---|---|---|---|
| L-isoleucine | 9.0 | | 0.0686 |
| L-leucine | 11.0 | | 0.0838 |
| L-valine | 8.4 | | 0.0717 |
| L-tryptophan | 0.75 | | 0.00367 |
| L-phenylalanine | 0.55 | | 0.00333 |
| L-tyrosine | 0.45 | | 0.00248 |
| L-lysine acetate | 8.6 | (base, 6.09) | 0.0417 |
| L-methionine | 1.0 | | 0.0067 |

| Amino Acid | g./l. | mole/l. |
|---|---|---|
| L-threonine | 4.5 | 0.0378 |
| L-alanine | 7.65 | 0.0858 |
| L-arginine | 6.0 | 0.0344 |
| L-histidine | 2.4 | 0.0155 |
| L-proline | 8.0 | 0.0695 |
| L-serine | 5.0 | 0.0476 |
| glycine | 9.0 | 0.120 |
| L-aspartic acid | 5.0 | 0.0376 |
| L-glutamic acid | 8.6 | 0.0585 |
| L-ornithine | 4.2 | 0.0318 |
| L-cysteine.HCl.H$_2$O | 0.2 | 0.00114 |

With respect to the formulations of Examples I to III, as a supplement to oral feeding, wherein this amino acid solution is preferentially infused into peripheral veins, i.e. arm or leg veins, an isotonic or near isotonic concentration of an amino acid solution having a composition within the specified ranges can be utilized. Thus a 3.0 to 5.0% w/v amino acid solution having the above composition can be used.

Another alternate route of administration for the solution is to administer all nutrients via a nasogastric tube or a jejunostomy tube. As in the I.V. administration, the amino acid solution is added to sufficient calories provides as carbohydrates and/or far, vitamins and minerals. The complete diet is then administered slowly over a 24 hour period.

EXAMPLE V

For oral consumption, the amino acid mixture, having the same molar ratios and the same ranges as described previously, 80 – 120% of the recommended daily allowance of essential minerals, sufficient calories in the form of monosaccharide, sugar and malto dextrins and/or fat are mixed with natural and/or synthetic food flavors such that reconstitution with water or gelatinous base yields an edible food preparation in the form of a palatable liquid drink or a semisolid food. A typical formulation of the principal ingredients of a food preparation is given below:

| Ingredient | %w/w | |
|---|---|---|
| Amino Acids | 9.23 | |
| L-isoleucine | | 1.01 |
| L-leucine | | 1.23 |
| L-valine | | 0.95 |
| L-tryptophan | | 0.08 |
| L-phenylalanine | | 0.11 |
| L-lysine acetate | | 0.96 |
| L-methionine | | 0.11 |
| L-threonine | | 0.50 |
| L-alanine | | 0.86 |
| L-arginine | | 0.67 |
| L-histidine | | 0.27 |
| L-proline | | 0.90 |
| L-serine | | 0.56 |
| glycine | | 1.00 |
| L-cysteine.HCl.H$_2$O | | 0.02 |
| Carbohydrates (Sugar Maltodextrin) | 77.8 | |
| Fat | 6.69 | |
| Citric Acid | 0.846 | |

| Ingredient | %w/w |
|---|---|
| Potassium Citrate | 0.419 |
| Calcium Glycerophosphate | 0.89 |
| Sodium Chloride | 0.470 |
| Potassium Sulfate | 0.194 |
| Potassium Phosphate, Dibasic | 0.182 |
| Magnesium Oxide | 0.0875 |
| Zinc Sulfate.H$_2$O | 0.0055 |
| Ferrous Sulfate | 0.00524 |
| Copper Gluconate | 0.002 |
| Manganous Sulfate.H$_2$O | 0.0011 |
| Potassium Iodide | 0.0000252 |
| Flavor or Color | 1.00 |

It will be understood that in the special oral amino acid diets for use in liver disease therapy, the pattern of amino acids is of critical importance. Calories as carbohydrates and/or fats, vitamins and minerals are also needed, but can be supplied in various forms. In the oral administration of amino acids to liver diseased patients, it may be desirable to sterilize the intestines by also orally administering an antibiotic such as Kanamycin. See Fischer et al., *Surgical Forum*, Vol. XXV, 369 (1974).

EXAMPLE VI

Following the procedure of Example V, the amino acids combined with the other components include:

| Amino Acid | %w/w |
|---|---|
| L-isoleucine | 9.20 |
| L-leucine | 11.25 |
| L-valine | 8.60 |
| L-tryptophan | 0.77 |
| L-phenylalanine | 0.56 |
| L-tyrosine | 0.46 |
| L-lysine acetate | 6.23 |
| L-methionine | 1.02 |
| L-threonine | 4.60 |
| L-alanine | 7.82 |
| L-arginine | 6.14 |
| L-histidine | 2.45 |
| L-proline | 8.18 |
| L-serine | 5.11 |
| glycine | 9.20 |
| L-aspartic acid | 5.11 |
| L-glutamic acid | 8.79 |
| L-ornithine | 4.29 |
| L-cysteine.HCl.H$_2$O | 0.22 |

The foregoing formulation will be combined with the other components set out in Example IV in from 5 to 10 parts by weight per the specified parts by weight of the other ingredients as set in Example IV. As will be noted therefore the total weight percent of amino acids in the complete formulation is a little greater than that of Example IV. However, the amino acids present in both formulations are included in substantially the same proportions with respect to each other.

EXAMPLE VII

Following the procedure of Example I, an alternate amino acid solution for liver disease therapy is prepared from the following pure crystalline essential amino acids and in the following concentrations:

| Amino Acid | g./l. | | mole/l. |
|---|---|---|---|
| L-isoleucine | 9.0 | | 0.0686 |
| L-leucine | 11.0 | | 0.838 |
| L-valine | 8.4 | | 0.0717 |
| L-tryptophan | 0.75 | | 0.00367 |
| L-phenylalanine | 0.55 | | 0.00333 |
| L-tyrosine | 0.45 | | 0.00248 |
| L-lysine acetate | 8.6 | (base, 6.09) | 0.0417 |
| L-methionine | 1.0 | | 0.00670 |
| L-threonine | 4.5 | | 0.0378 |
| L-alanine | 7.65 | | 0.0858 |
| L-arginine | 6.0 | | 0.0344 |
| L-histidine | 2.4 | | 0.0155 |
| L-proline | 8.0 | | 0.0695 |
| L-serine | 5.0 | | 0.0476 |
| glycine | 9.0 | | 0.120 |
| L-aspartic acid | 5.0 | | 0.0376 |
| L-glutamic acid | 8.6 | | 0.0585 |
| L-ornithine | 4.2 | | 0.0318 |
| L-cysteine.HCl.H$_2$O | 0.2 | | 0.00114 |

We claim:

1. An amino acid formulation for administration to human patients with liver disease, comprising a mixture of the following essential and nonessential amino acids combined in proportions defined by the following interrelated molar ranges:

| Amino Acids | Molar Ranges |
|---|---|
| L-isoleucine | 0.0549–0.0823 |
| L-leucine | 0.0670–0.101 |
| L-valine | 0.0574–0.0861 |
| L-tryptophan | 0.000816–0.00441 |
| L-phenylalanine | 0–M |
| L-tyrosine | 0–0.00300 |
| L-lysine | 0.0333–0.0500 |
| L-methionine | 0.00491–0.0147 |
| L-threonine | 0.0228–0.0454 |
| L-alanine | 0.0686–0.103 |
| L-arginine | 0.0275–0.0413 |
| L-histidine | 0.0124–0.0186 |
| L-proline | 0.0556–0.00834 |
| L-serine | 0.0152–0.0571 |
| glycine | 0.0451–0.144 |
| L-aspartic acid | 0–0.0451 |
| L-glutamic acid | 0–0.0702 |
| L-ornithine | 0–0.0382 |
| L-cysteine | 0–0.00228 | wherein M represents the upper limit of the range for phenylalanine and is equal to 0.009 minus the respective molar amount of tyrosine present in said mixture, the combined molar amounts of phenylalanine and tyrosine being at least equal to 0.002 on the same respective molar basis, the respective molar proportions of isoleucine, leucine, valine, tryptophan, phenylalanine, and tyrosine being selected from the above molar ranges thereof so that the ratio of the combined molar proportions of isoleucine, leucine, and valine to (a) the molar proportion of tryptophan is within the numerical range from 40 to 300, and to (b) the combined molar proportion of phenylalanine and tyrosine is within the numerical range from 15 to 135.

2. The amino acid formulation of claim 1 in which said ratio with respect to (a) is from 50 to 90, and said ratio with respect to (b) is from 30 to 50.

3. The amino acid formulation of claim 1 in which said mixture of amino acids is dissolved in a sterile aqueous solution havng a total amino acid concentration of from 2 to 9 weight percent based on the solution.

4. The amino acid formulation of claim 3 in which said ratio with respect to (a) is from 50 to 90, and said ratio with respect to (b) is from 30 to 50.

5. The amino acid formulation of claim 1 prepared as an edible food for oral administration.

6. The method of supplying amino acids to a human patient having a diseased liver, comprising administering to said patient the amino acid formulation defined in claim 1.

7. The method of claim 6 in which said amino acid formulation is administered in an amount equivalent to at least 50 grams protein per patient per 24 hours.

8. The method of claim 7 in which said mixture of amino acids as defined in claim 1 is in the form of an aqueous solution of said amino acids and in which said solution is administered by intravenous infusion.

9. The method of claim 7 in which said mixture of amino acids as defined in claim 1 is administered by oral feeding.

10. An intravenous infusion solution of amino acids for administration to human patients with liver disease, consisting essentially of a sterile aqueous solution of the following essential and nonessential amino acids in the following moles per liter of solution concentrations:

| Amino Acids | Concentrations |
| --- | --- |
| L-isoleucine | 0.0549–0.0823 |
| L-leucine | 0.0670–0.0101 |
| L-valine | 0.0574–0.0861 |
| L-tryptophan | 0.000816–0.00441 |
| L-phenylalanine | 0.00444–0.0133 |
| L-lysine | 0.0333–0.0500 |
| L-methionine | 0.00491–0.0147 |
| L-threonine | 0.0228–0.0454 |
| L-alanine | 0.0686–0.103 |
| L-arginine | 0.0275–0.0413 |
| L-histidine | 0.0124–0.0186 |
| L-proline | 0.0556–0.0834 |
| L-serine | 0.0152–0.0571 |
| glycine | 0.0451–0.144 |
| L-cysteine | 0–0.00228 | the respective concentrations of isoleucine, leucine, valine, tryptophan, and phenylalanine being selected from the above concentration ranges therefor so that the ratio of the total moles per liter of isoleucine, leucine, and valine to (a) the respective concentration of tryptophan is within the numerical range for said ratio of 50 to 90, and to (b) the respective concentration of phenylalanine is within the numberical range for said ratio of 30 to 50.

11. The method of supplying amino acids to a human patient having a diseased liver, comprising intravenously infusing said patient with the amino acid solution defined by claim 10.

12. The method of claim 11 in which said solution is infused in an amount equivalent to at least 50 grams protein per patient per 24 hours.

13. The intravenous infusion solution of claim 8 in which said ratio with respect to (a) is from 50 to 90, and said ratio with respect to (b) is from 30 to 50.

14. An amino acid preparation for oral administration to human patients with liver disease containing carbohydrate and/or fat nutrients together with a mixture of the following essential and nonessential amino acids combined in proportions defined by the following interrelated molar ranges:

| Amino Acids | Molar Ranges |
| --- | --- |
| L-isoleucine | 0.0549–0.0823 |
| L-leucine | 0.0670–0.101 |
| L-valine | 0.0574–0.0861 |
| L-tryptophan | 0.000816–0.00441 |
| L-phenylalanine | 0–M |
| L-tyrosine | 0–0.00300 |
| L-lysine | 0.0333–0.0500 |
| L-methionine | 0.00491–0.0147 |
| L-threonine | 0.0228–0.0454 |
| L-alanine | 0.0686–0.103 |
| L-arginine | 0.0275–0.0413 |
| L-histidine | 0.0124–0.0186 |
| L-proline | 0.0556–0.00834 |
| L-serine | 0.0152–0.0571 |

| Amino Acids | Molar Ranges |
| --- | --- |
| glycine | 0.0451–0.144 |
| L-aspartic acid | 0–0.0451 |
| L-glutamic acid | 0–0.0702 |
| L-ornithine | 0–0.0382 |
| L-cysteine | 0–0.00228 | wherein M represents the upper limit of the range for phenylalanine and is equal to 0.009 minus the respective molar amount of tyrosine present in said mixture, the combined molar amounts of phenylalanine and tyrosine being at least equal to 0.002 on the same respective molar basis, the respective molar proportions of isoleucine, leucine, valine, tryptophan, phenylalanine, and tyrosine being selected from the above molar ranges thereof so that the ratio of the combined molar proportions of isoleucine, leucine, and valine to (a) the molar proportion of tryptophan is within the numerical range from 40 to 300, and to (b) the combined molar proportion of phenylalanine and tyrosine is within the numerical range from 15 to 135.

* * * * *

UNITED STATES PATENT AND TRADEMARK OFFICE
CERTIFICATE OF CORRECTION

PATENT NO. : 3,950,529
DATED : April 13, 1976
INVENTOR(S) : Josef E. Fischer et al.

It is certified that error appears in the above—identified patent and that said Letters Patent is hereby corrected as shown below:

In Claims 1 and 14, the Molar range for L-proline should read "0.0556 - 0.0834".

Signed and Sealed this

Fifteenth Day of June 1982

[SEAL]

Attest:

Attesting Officer

GERALD J. MOSSINGHOFF

Commissioner of Patents and Trademarks